United States Patent [19]

Kennedy et al.

[11] 4,157,572

[45] Jun. 5, 1979

[54] SUPERIMPOSITION OF TELEVISION IMAGES

[75] Inventors: William H. Kennedy, Monroeville; Donald Sashin, Pittsburgh, both of Pa.

[73] Assignee: University of Pittsburgh, Pittsburgh, Pa.

[21] Appl. No.: 832,020

[22] Filed: Sep. 12, 1977

[51] Int. Cl.² ............... G11B 5/78; G11B 31/00; H04N 7/18

[52] U.S. Cl. ............................ 360/33; 358/111; 358/183

[58] Field of Search ............ 360/33, 79; 358/111, 358/105, 93, 4, 12, 183

[56] References Cited

U.S. PATENT DOCUMENTS

| 3,673,317 | 6/1972 | Newell et al. | 358/111 |
|---|---|---|---|
| 3,745,245 | 7/1973 | Yunde et al. | 358/111 |
| 3,894,181 | 7/1975 | Mistretta et al. | 358/111 |
| 3,919,467 | 11/1975 | Peugeot | 358/111 |
| 3,961,133 | 6/1976 | Bennett | 358/183 |

*Primary Examiner*—Alfred H. Eddleman
*Attorney, Agent, or Firm*—Arnold B. Silverman

[57] ABSTRACT

Apparatus for the superimposition of television images including recorder apparatus for recording and playing back first video signals, image generating apparatus for providing second video signals, drive apparatus for driving the image generating apparatus synchronously with respect to the recorder apparatus responsive to receipt by the drive apparatus of first video signals and signal combining apparatus for superimposing the first and second video signals. Display and/or recording means may be provided for displaying and recording the superimposed video image.

12 Claims, 5 Drawing Figures

SUPERIMPOSITION OF TELEVISION IMAGES

BACKGROUND OF THE INVENTION

1. Field of the Invention

This invention relates to apparatus for superimposition of television images and, more specifically, such apparatus which is adapted to provide stable superimposition to produce an improved representation of superimposed live television and recorded images.

2. Description of the Prior Art

Various systems for employing electronic processing of image data have been known. See, for example, U.S. Pat. Nos. 3,961,133 and 4,011,401.

It has also been known that a recorded image may advantageously be combined with a real-time or live television image in order to provide for more efficient use of image data. In many uses of such systems, there is a great need for high quality equipment so as to provide images devoid of distortion or misrepresentation of the spatial information. For example, in the medical environment, it has been known to employ a subtraction concept to provide an image of enhanced quality through deletion of bones or other fixed objects from the final image. It has also been known to employ superimposition as a means for more effective catheterization techniques. In such use, an image of a blood vessel with its branches may be superimposed upon an image of a catheter. Such uses are disclosed in an article entitled "Electronic Radiography in Stereotaxic Thrombosis of Intracranial Aneurysms and Catheter Embolization of Cerebral Arteriovenous Malformations" which appears at pages 359–363 in Volume 105, No. 2 issue of *Radiology*, (Nov. 1972).

One of the problems encountered with such systems for coordinating the superimposition of a live television image with previously recorded video disc information has been the need for a very highly stabilized magnetic disc recorder including feedback circuits. Such a system requires a very costly and complex disc system which is relatively expensive to maintain, is heavy and provides, in spite of precautions, inherent instability that results in some degree of undesired misregistration (such as 200–400 nanosecond jitter, for example). The discs employed in such systems inherently result in some degree of localized variation in disc velocity. By contrast, in such a system, the video signal which is generated by a television camera is generally rather stable (such as 10–50 nanosecond jitter, for example).

There remains, therefore, a specific need for apparatus which may economically and more effectively provide for superimposition of recorded images with television images in a fashion which reduces the misregistration on the displayed or recorded image.

SUMMARY OF THE INVENTION

The present invention has solved the above-described problems by providing an economical, light-weight and efficient system for minimizing the misregistration in the superimposition of real-time television images with recorded images. In the system of the present invention, a prerecorded composite image on the disc recorder is used to synchronously drive the television camera (or other image generation means). In this fashion, any variations in velocity of the recorder and resultant variations in timing during playback are not corrected but are fed to the television camera to make the camera track the timing of the disc recorder. Signal combining means are provided for superimposing the first video image signal emitted by the recorder means and the second video image signal emitted by the television camera. The recorder means may advantageously be a video disc recorder. The signal combining means may include adder circuit means for producing composite video signals and reverse polarity circuit means for reversing video signals. The composite video signals may advantageously be presented on a television monitor, may be photographed by a camera, may be recorded on means such as a video tape or disc recorder.

It is an object of this invention to provide apparatus which in economical and reliable fashion permits stable superimposition of a television image with a prerecorded image while maintaining precise registration therebetween.

It is a further object of this invention to provide such apparatus which not only will provide improved image quality in respect of superimposed images but also will provide a simple, easy to maintain system.

It is another object of this invention to provide a system which permits recording or viewing of subtracted or superimposed video images on relatively inexpensive magnetic disc or tape recorders, as well as other means.

These and other objects of the invention will be more fully understood from the following description of the invention on reference to the illustrations appended hereto.

DESCRIPTION OF THE PREFERRED EMBODIMENTS

Figure 1:
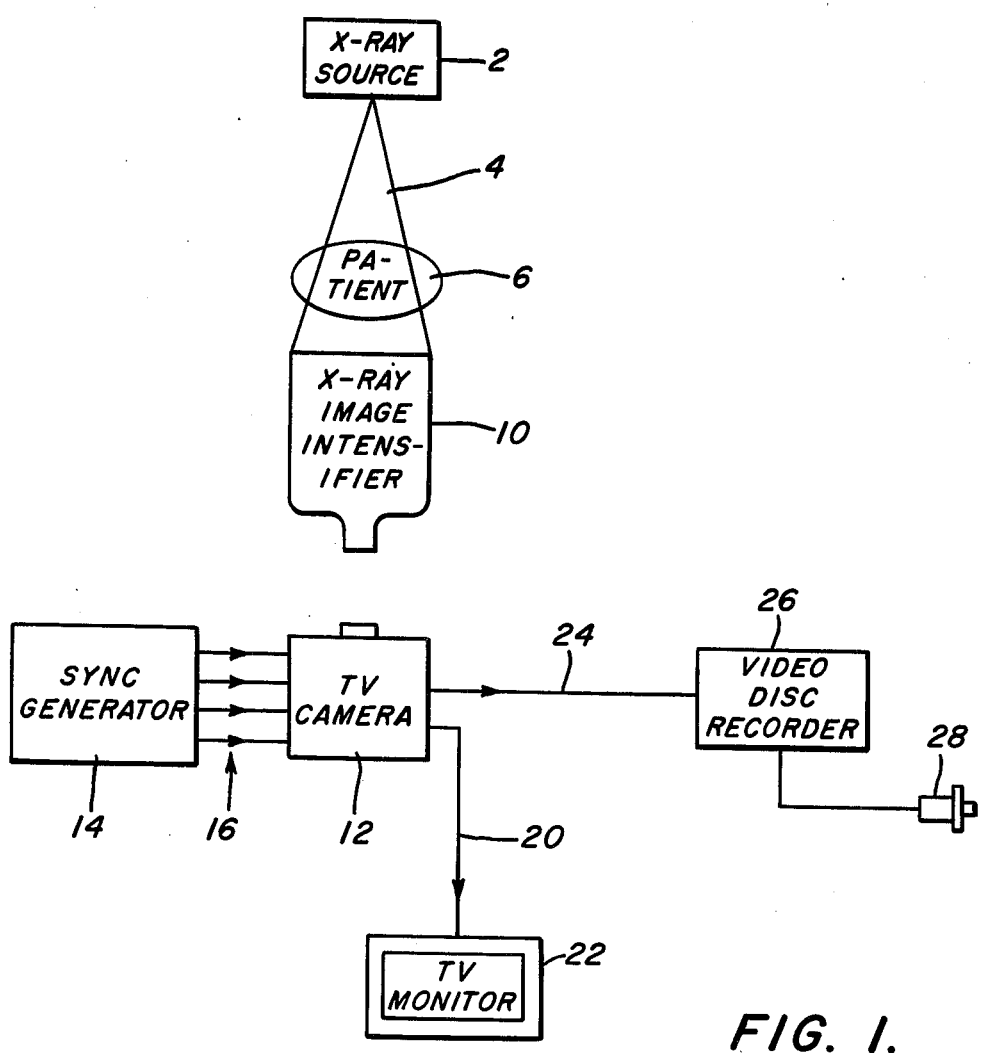
FIG. 1 is a schematic illustration of a means for establishing a record of a video image.

Referring now more specifically to FIG. 1, there is shown a system for creating a recording of a video image. In the example illustrated in FIG. 1, use in a medical radiography environment is shown. A radiation source, such as x-ray source 2, emits a conical beam 4, which impinges upon patient 6 and has a portion thereof pass through the patient 6 and impinge upon x-ray image intensifier 10. Image generation means, in the form of television camera 12, receives the output of image intensifier 10 which serves to convert the received x-ray into a visual image which may be received by the television camera 12. External sync generator 14 provides over leads, (generally indicated by the reference number 16) horizontal drive pulses, vertical drive pulses, blanking pulses and sync pulses to television camera 12. The video signal emitted by the television camera 12 over lead 20 is delivered to television monitor 22 for visual display of the image. The video signal emitted by the television camera 12 is also, by means of lead 24, delivered to recorder means, which, in the form shown, may be a disc recorder 26. Switch 28 is employed as a means of operating recorder 26 when it is desired to record a particular video image. The user, therefore, may have the hand-operable switch 28 in hand while viewing television monitor 22 and may initiate and terminate recording the video image displayed on 22 by means of switch 28. The apparatus shown in FIG. 1 is an example of a means of establishing a stored video image and forms no part of the present invention, per se, but it is compatible therewith and adapted for use in establishing superimposed images in accordance with the present invention.

Figure 2:
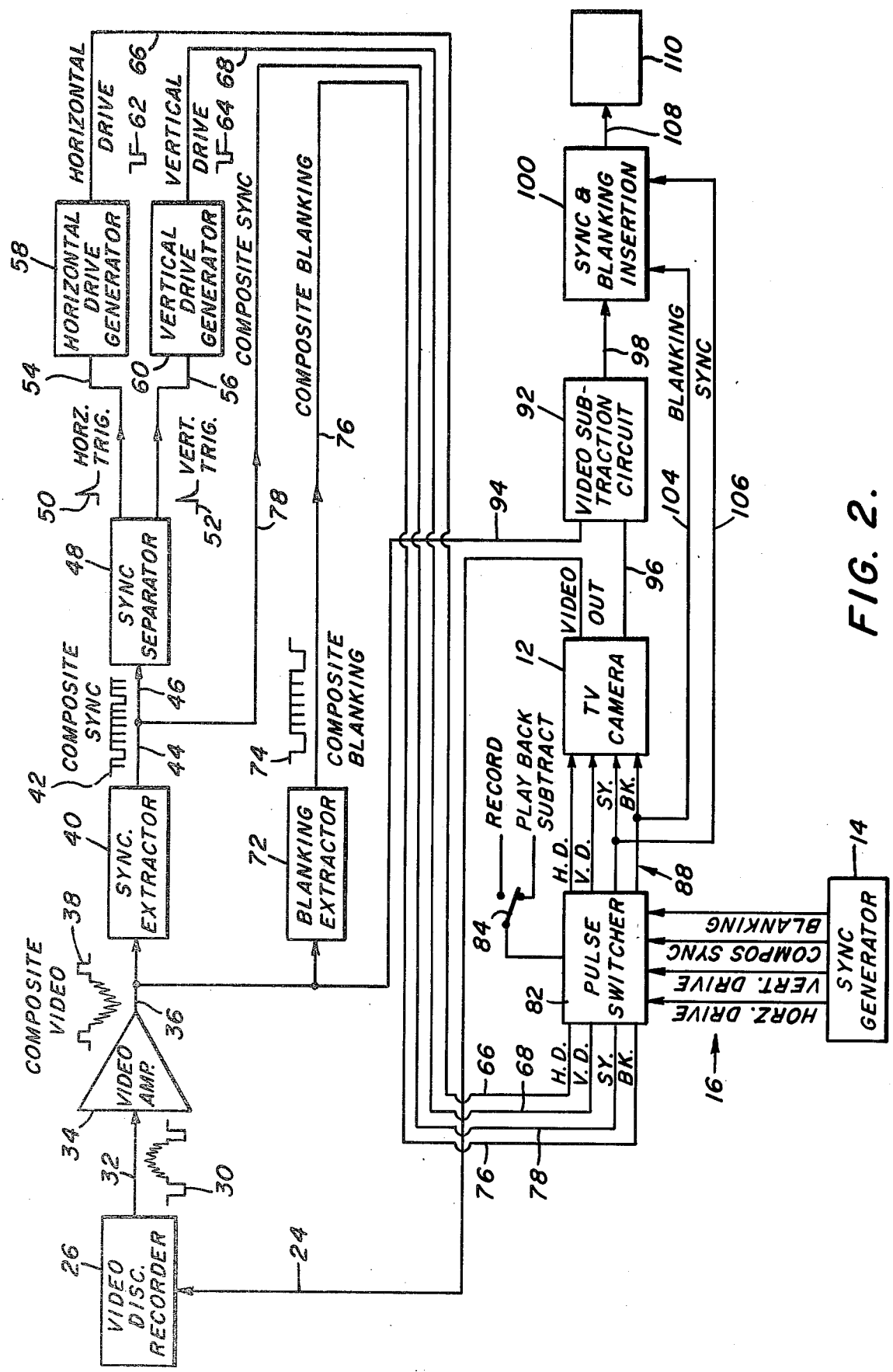
FIG. 2 is a schematic illustration of a form of the system of the present invention.

Referring now to FIG. 2, the present invention will now be considered in greater detail. As the source of the live image, which the television camera is receiving, forms no part of the present invention, per se, the radiation source 2, patient 6 and x-ray imaging intensifier 10, shown in FIG. 1, have not been shown in FIG. 2.

Referring still to FIG. 2, the manner in which the present invention permits the use of recorder means which is relatively inexpensive and easy to maintain will now be considered. For purposes of considering this figure, it will be assumed that the recorder means 26 is a disc recorder having a previously recorded image which, when playback is initiated, will result in the recorder 26 emitting a first video signal. It will also be assumed that the television camera is receiving an image and emits a continuous second video signal. It is desired to superimpose the first and second video signals.

The term "superimposition" as used herein shall refer to the electronic superimposition of two images while maintaining the content of the images in respect of spatial distribution and permitting elimination or minimization of certain portions of one or both images through alteration of relative brightness thereof. This term shall expressly include the subtraction or addition or two or more images.

The composite video signal 30 (a signal containing video, sync and blanking) from the disc recorder 26 is delivered over lead 32 to amplifier 34. The signal 30 is amplified and the amplified signal 38 is fed by lead 36 to the sync extractor 40, which provides composite sync output signal 42 on lead 44. This composite sync signal 42 (which contains both horizontal sync and vertical sync) is then fed by leads 44, 46 to a sync separator 48. The sync separator 48 generates a separate horizontal trigger signal and vertical trigger signal over leads 54, 56, respectively, to horizontal drive generator 58 and vertical drive generator 60, respectively. These trigger signals are used to generate standard width drive signals 62, 64 over leads 66, 68, respectively.

The composite video signal 38 from video amplifier 34 is also fed to blanking extractor 72 which, in turn, provides composite blanking output signal 74 on lead 76.

The pulse switcher 82 has a switch which permits use of the pulse switcher 82 in a record mode or in a playback-subtract mode. In the record mode, as was described in connection with FIG. 1, the external sync generator 14 (which may advantageously be a EIA-RS170 sync generator) emits drive signals over leads 16 which pass through pulse switcher 82 to television camera 12 by leads 88. The output of television camera 12 is fed to video disc recorder 26 by lead 24 for recording.

In operating the system in the playback-subtract mode, switch 84 is moved to the proper position. In this mode, pulse switcher 82 permits the four drive signals received on leads 66, 68, 76, 78 to be fed to the television camera over leads 88. The recorded composite video signal from video amplifier 34 is fed to the video subtraction circuit 92 by lead 94 to provide the recorded input. The line composite video signal from the television camera 12 is fed to the subtraction circuit 92 by lead 96. One of the two video signals introduced into the video subtraction circuit 92 on leads 94, 96 is inverted in the subtraction circuit 92 and then added to the other video signal, thereby cancelling all but the difference between the two video signals. Means are provided either in the video subtraction circuit 92 or cooperating therewith to permit determination of the fraction of each video signal which is added to produce the video signal emitted on lead 98. In addition, the output video signal can be adjusted. The resultant difference signal is a noncomposite video signal as the sync and blank are also cancelled. This noncomposite signal is fed by lead 98 to sync and blanking insertion circuit 100. Stripped, sync and blanking signals from leads 88 are connected by leads 104, 106 to the sync and blanking insertion circuit 100. The output signal of the sync and blanking insertion circuit 100 on lead 108 is a composite video signal which is fed to video signal receiving means 110. The video signal receiving means 110 may be provided in the form of a monitor or storage device, such as a television or other monitor, a video tape recorder, a video disc recorder, a photographic camera, electron storage tube or digital memory, or any other display or recording device capable of handling the disc timing variations.

Figure 3:
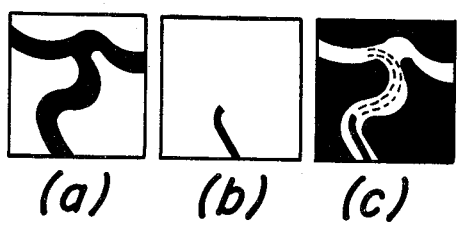
FIGS. 3(*a*), (*b*) and (*c*) are illustrations of the manner in which images may be superimposed by the present invention.

Referring now to FIG. 3, the use of the foregoing technique in achieving rapid and accurate placement of a catheter will now be considered. FIG. 3(a) may be considered as the first video signal which has been previously recorded. It illustrates a main blood vessel and its branches. FIG. 3(b) can be considered to be the second video signal which is obtained from the live television camera and shows a catheter. In the context of the present invention, replay of the recorded image shown in FIG. 3(a) serves to drive the television camera and generate the image shown in FIG. 3(b). Processing by the system shown in FIG. 2 would result in initial reversal of the image of 3(a) to provide it as shown in FIG. 3(c), and the superimposition electronically of the catheter shown in FIG. 3(b). This results in the individual operating the catheter having a specific image as to its exact positioning in a very clear fashion which permits rapid and accurate placement of the catheter. Such an approach could readily be employed with the placement of electrodes, needles and other items employed in a medical environment, as well as for numerous other medical and nonmedical uses.

It will therefore be appreciated that the present invention provides an economical means of employing conventional, inexpensive equipment which is durable in nature and yet adapted to provide resistance to misregistration in the stable superimposition of television images. All of this is accomplished avoiding the need to provide large, heavy, magnetic discs and expensive digital time base correctors and expensive means for compensating for velocity variations in attempting to coordinate an image signal stored on a magnetic disc recorder with those obtained from a live television camera. The present invention involves providing driving means which respond effectively to the output of the magnetic disc recorder and serve to drive the television camera. As a result, automatic coordination is obtained in this simple and reliable fashion.

While for convenience of reference herein, discussion has centered around uses in specific medical environments, it will be appreciated that the invention may be advantageously employed in other environments, such as other medical uses, nondestructive testing and the entertainment industry.

While emphasis herein has been placed upon use of image generating means in the form of a television camera, it will be appreciated that the invention is adapted for use with other devices generating video signals, including, for example, a magnetic disc recorder, electron storage tube or digital memory.

Whereas particular embodiments of the invention have been described above for purposes of illustration, it will be appreciated by those skilled in the art that numerous variations of the details may be made without departing from the invention as described in the appended claims.

We claim:

1. Apparatus for the superimposition of television images comprising
   recorder means for recording and playing back composite first video signals,
   image generating means for providing second video signals,
   drive means for driving said image generating means synchronously with respect to said recorder means responsive to receipt by said drive means of said first video signal,
   said drive means including circuit means for separating from said composite first video signals, horizontal drive, vertical drive, sync and blanking signals and feeding said separated signals to said image generating means to thereby effect control of the operation of said image generating means by said recorder means, and
   signal combining means for superimposing said first and second video signals.

2. The apparatus of claim 1 wherein said recorder means includes a video disc recorder.

3. The apparatus of claim 1 wherein said signal combining means includes means for reversing one of the video signals received thereby prior to combining said signals.

4. The apparatus of claim 1 wherein said image generating means is a television camera.

5. The apparatus of claim 2 including video image signal receiving means operatively associated with said signal combining means for receiving said composite video signals.

6. The apparatus of claim 5 wherein said video image signal receiving means includes means for recording said composite video signal.

7. The apparatus of claim 1 including said drive means having
   amplifier means for amplifying the signal from said recorder means,
   sync extractor means operatively associated with said amplifier means for generating a composite sync signal, and
   blanking extractor means operatively associated with said amplifier means for generating a composite blanking signal.

8. The apparatus of claim 7 including
   said circuit means having sync separator means operatively associated with said sync extractor means for generating horizontal and vertical trigger signals,
   horizontal drive generator means operatively associated with said sync separator means for generating horizontal drive signals, and
   vertical drive generator means operatively associated with said sync separator means for generating vertical drive signals.

9. The apparatus of claim 8 including
   said drive means having means for introducing said composite sync signals, said composite blanking signals, said horizontal drive signals and said vertical drive signals into said image generating means.

10. The apparatus of claim 9 including
    said means for introducing said sync, blanking and drive signals into said image generating means including switch means for permitting drive signals from an external sync generator to be introduced into said image generating means in lieu of said sync, blanking and drive signals from said drive means.

11. The apparatus of claim 3 including said signal combining means having means for providing a noncomposite combination of said video signals.

12. The apparatus of claim 11 including said signal combining means having sync and blanking insertion means for converting said noncomposite combination into a composite signal by introduction of sync and blanking signals.

* * * * *

UNITED STATES PATENT AND TRADEMARK OFFICE
CERTIFICATE OF CORRECTION

PATENT NO. : 4,157,572
DATED : June 5, 1979
INVENTOR(S) : William H. Kennedy and Donald Sashin It is certified that error appears in the above—identified patent and that said Letters Patent are hereby corrected as shown below:

Column 1, line 20, change "misrepresentation" to --misregistration--.

Column 3, line 29, before "two" change "or" to -- of --.

Signed and Sealed this

Twenty-seventh Day of November 1979

[SEAL]

Attest:

RUTH C. MASON
Attesting Officer

LUTRELLE F. PARKER
Acting Commissioner of Patents and Trademarks